(12) United States Patent
Spiegel

(10) Patent No.: US 10,890,518 B2
(45) Date of Patent: *Jan. 12, 2021

(54) SUBSTRATE SEAL TEST METHOD AND APPARATUS

(71) Applicant: James Joseph Spiegel, Aliso Viejo, CA (US)

(72) Inventor: James Joseph Spiegel, Aliso Viejo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/733,784

(22) Filed: Jan. 3, 2020

(65) Prior Publication Data

US 2020/0141854 A1  May 7, 2020

Related U.S. Application Data

(63) Continuation-in-part of application No. 16/110,289, filed on Aug. 23, 2018, now Pat. No. 10,571,383.

(60) Provisional application No. 62/597,403, filed on Dec. 11, 2017.

(51) Int. Cl.
*E04G 23/02* (2006.01)
*G01N 15/08* (2006.01)
*G01M 3/28* (2006.01)
*G01N 33/38* (2006.01)

(52) U.S. Cl.
CPC ..... *G01N 15/0826* (2013.01); *E04G 23/0211* (2013.01); *G01M 3/2869* (2013.01); *G01N 33/383* (2013.01)

(58) Field of Classification Search
CPC ................ G01N 15/082; G01N 33/383; E04G 23/0211; E04G 23/0203; E01C 7/147; Y10T 29/49732; Y10T 29/49734; Y10T 29/49746; Y10T 29/49764; Y10T 29/49771
USPC ............ 52/514.5; 156/71, 64; 73/38, 40, 46, 73/49.8
See application file for complete search history.

(56) References Cited

U.S. PATENT DOCUMENTS

| | | | | |
|---|---|---|---|---|
| 1,989,695 A | * | 2/1935 | Jensen | B23P 6/04 29/402.11 |
| 2,125,785 A | * | 8/1938 | Hill, Jr. | E01C 23/10 404/78 |
| 2,951,506 A | * | 9/1960 | Diperstein | B23P 6/04 138/99 |
| 2,998,645 A | * | 9/1961 | Diperstein | B23P 6/04 29/402.11 |
| 3,352,812 A | * | 11/1967 | Parham, Jr. | C08L 81/00 524/432 |

(Continued)

OTHER PUBLICATIONS

Alchemy-Spetec, Leak-Seal Product Line, Mechanical Packer and Accessories Brochure.‡

(Continued)

*Primary Examiner* — Kyle J. Walraed-Sullivan
(74) *Attorney, Agent, or Firm* — Klein, O'Neill & Singh, LLP

(57) ABSTRACT

A method for testing whether a sealing method is effective may include the steps of testing a flow characteristic of the substrate, sealing the substrate, re testing the flow characteristic of the substrate, then comparing the before and after flow characteristics of the substrate to determine whether the sealing step was effective or to quantify a sealing effectiveness to the sealing step.

13 Claims, 14 Drawing Sheets

(56) References Cited

U.S. PATENT DOCUMENTS

| | | | | |
|---|---|---|---|---|
| 3,618,520 A * | 11/1971 | Hamasaki | | F42D 1/00 102/313 |
| 4,067,759 A * | 1/1978 | Vrolyk | | B29C 44/184 138/97 |
| 4,352,262 A * | 10/1982 | Edelmann | | E04G 23/0211 52/742.16 |
| 4,360,994 A * | 11/1982 | Hodges | | E04G 23/0211 52/742.16 |
| 4,430,841 A * | 2/1984 | Yamaguchi | | E04G 23/0203 52/742.16 |
| 4,509,884 A * | 4/1985 | Trout | | E04G 23/0211 405/269 |
| 4,512,123 A * | 4/1985 | Fischer | | E04G 23/0211 52/514.5 |
| 4,531,403 A * | 7/1985 | de Korompay | | E21B 47/10 73/37 |
| 4,536,417 A * | 8/1985 | Shimizu | | C04B 41/009 427/140 |
| 4,798,502 A * | 1/1989 | Trout | | E04F 21/165 405/269 |
| 4,845,828 A * | 7/1989 | Reed | | B23P 6/04 29/402.15 |
| 5,129,135 A * | 7/1992 | Yoshino | | E04G 23/02 29/402.14 |
| 5,257,486 A * | 11/1993 | Holmwall | | B05C 7/00 52/514.5 |
| 5,465,881 A * | 11/1995 | Zwicky | | B63C 11/52 222/389 |
| 5,476,340 A * | 12/1995 | Contrasto | | E01C 7/147 264/35 |
| 5,476,344 A * | 12/1995 | Nordvall | | E04G 23/0203 405/269 |
| 5,536,353 A * | 7/1996 | Fonseca | | F16L 59/16 138/89 |
| 5,555,691 A * | 9/1996 | Nguyen | | E04G 23/0203 52/514 |
| 5,771,557 A * | 6/1998 | Contrasto | | E01C 7/147 264/36.2 |
| 6,226,948 B1 * | 5/2001 | Trout | | E04G 23/0211 52/514.5 |
| 6,332,350 B1 * | 12/2001 | Inoue | | G01M 3/20 73/40 |
| 9,528,286 B2 ‡ | 12/2016 | Wheatley | | E04G 23/0214 |
| 10,494,826 B1 * | 12/2019 | Wheatley | | E04G 23/024 |
| 2001/0054474 A1 * | 12/2001 | Braun | | E04G 23/0203 156/94 |
| 2003/0215603 A1 * | 11/2003 | Lee | | C09J 7/21 428/134 |
| 2005/0120660 A1 * | 6/2005 | Kim | | E04G 23/0203 52/514 |
| 2005/0176529 A1 * | 8/2005 | Frischmon | | A63B 59/70 473/560 |
| 2006/0010826 A1 * | 1/2006 | Canteri | | E04G 23/0218 52/741.4 |
| 2007/0062630 A1 * | 3/2007 | Wilbur | | A63B 60/42 156/94 |
| 2007/0249779 A1 * | 10/2007 | Dellandrea | | C04B 41/483 524/502 |
| 2008/0261027 A1 * | 10/2008 | Li | | C04B 28/04 428/332 |
| 2010/0137473 A1 * | 6/2010 | Carelli | | C04B 26/14 523/130 |
| 2014/0013833 A1 * | 1/2014 | Hosoda | | G01N 9/36 73/73 |
| 2014/0137503 A1 * | 5/2014 | Wheatley | | E04G 23/0211 52/514.5 |
| 2014/0248460 A1 * | 9/2014 | Taverne | | C04B 41/53 428/63 |
| 2014/0326168 A1 * | 11/2014 | Tanaka | | C04B 28/04 106/816 |
| 2015/0068154 A1 * | 3/2015 | Merlob | | E04G 23/0203 52/741.1 |
| 2015/0300033 A1 * | 10/2015 | Weber | | E04C 5/162 52/514 |
| 2016/0090328 A1 * | 3/2016 | Wiktor | | C04B 41/455 106/615 |
| 2018/0172662 A1 * | 6/2018 | Sasson | | G06T 7/0004 |
| 2019/0010719 A1 * | 1/2019 | Secrest | | E04G 23/0288 |
| 2019/0180105 A1 * | 6/2019 | Sasson | | G06F 16/583 |

OTHER PUBLICATIONS

Alchemy-Spetec, Spetec I.T.S. Kit, Two Component Polyurethane System, Revised May 22, 2018.‡

Sealboss Corp. USA, SealBoss® DataPort System® Product Data Sheet, Revised May 2017.‡

* cited by examiner
‡ imported from a related application

SUBSTRATE SEAL TEST METHOD AND APPARATUS

CROSS-REFERENCE TO RELATED APPLICATIONS

The present application is a continuation in part application to U.S. patent application Ser. No. 16/110,289, filed on Aug. 23, 2018, which claims priority to U.S. Provisional Application No. 62/597,403 filed on Dec. 11, 2017, the disclosures of which are expressly incorporated herein by reference.

STATEMENT RE: FEDERALLY SPONSORED RESEARCH/DEVELOPMENT

Not Applicable

BACKGROUND

1. Technical Field

The present disclosure relates generally to water sealing a porous concrete structure, and more specifically to crack filling and porous structure sealing systems and methods which allow for testing of crack filling effectiveness.

2. Description of the Related Art

There may be various deficiencies in measuring the effectiveness of crack filling in concrete structures, including primarily relying on observation when there is a range of influencing variable factors, such as crack geometry, water sources, hydrostatic pressure, and type of filling substance.

Accordingly, there is a need in the art for crack filling applications that improve on measuring the effectiveness of filling. Various aspects of the present disclosure address this particular need, as will be discussed in more detail below.

BRIEF SUMMARY

In accordance with one embodiment of the present disclosure, there may be provided a method of filling a crack in a concrete structure, where the crack may extend into the concrete structure from a first surface. The method may include a step of forming a first drill hole in the concrete structure. The first drill hole may extend into the concrete structure from the first surface to the crack and have an end at the first surface spaced from the crack. The method may include another step of forming a test hole in the concrete structure in spaced relation to the first drill hole. The test hole may extend into the concrete structure from the first surface to the crack and have an end at the first surface spaced from the crack. The method may include another step of conducting a baseline flow test by directing a test liquid into the test hole to determine at least one baseline liquid flow characteristic. The method may include another step of injecting a filling substance into the first drill hole and into the crack to at least partially fill the crack. The method may include another step of conducting a quality flow test by directing the test liquid into the test hole to determine at least one quality liquid flow characteristic following hardening of the filling substance in the crack.

The method may include another step of comparing the at least one baseline liquid flow characteristic to the at least one quality liquid flow characteristic to determine an effectiveness of the injecting step.

The method may include another step of forming a second drill hole in the concrete structure on an opposite side of the crack relative to the first drill hole. The second drill hole may extend into the concrete structure from the first surface to the crack and have an end at the first surface spaced from the crack. The method may include another step of injecting a filling substance into the second drill hole and into the crack.

The first drill hole may be formed by drilling into the concrete at an angle relative to the first surface that is non-orthogonal to the first surface.

The test liquid may be water directed into a test hole, and the baseline liquid flow characteristic may be a baseline flow rate, $Q_1$, and a baseline pressure, $P_1$, of the water flow through the test hole. The test liquid may be water directed into a test hole, and the quality liquid flow characteristic may be a quality flow rate, $Q_2$, and a baseline pressure, $P_2$, of the water flow through the test hole. The comparison may be between a baseline ratio, $Q_1/P_1$, and a quality ratio, $Q_2/P_2$.

In accordance with another embodiment of the present disclosure, the method may include another step of inserting a plug into the test hole. The plug may extend at least partially into the crack when inserted into the test hole. The method may include another step of removing the plug from the test hole after the step of injecting the filling substance into the first drill hole.

In accordance with another embodiment of the present disclosure, there may be a method of filling a crack in a concrete structure with a tube residing inside the crack. The method may include a step of conducting a baseline flow test by directing a test liquid into the crack via the tube. The method may include another step of injecting a filling substance into the crack via the tube to at least partially fill the crack. The method may include another step of conducting a quality flow test by directing the test liquid into the crack via the tube following hardening of the filling substance in the crack.

The baseline flow test may include directing water into the crack via the tube to determine a baseline flow rate, $Q_1$, and a baseline pressure, $P_1$, of the water flow through the crack. Conducting a quality flow test may include directing water into the crack via the tube to determine a quality flow rate, $Q_2$, and a baseline pressure, $P_2$, of the water flow through the crack. There may be another step of comparing a baseline ratio, $Q_1/P_1$, to a quality ratio, $Q_2/P_2$.

The method may include another step of cleaning inside the tube prior to the filling substance hardening.

In accordance with another embodiment of the present disclosure, there may be a step of forming a dead hole that extends into the concrete structure from the first surface and has an end between the first surface and a second surface. The distance between the first surface and the second surface may define a thickness of the concrete structure. Conducting a baseline flow test may include directing water into the dead hole to determine a baseline flow rate, $Q_1$, and a baseline pressure, $P_1$, of the water flow through the dead hole.

The present disclosure will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which.

Common reference numerals are used throughout the drawings and the detailed description to indicate the same elements. Moreover, the same element for the second embodiment as in the first embodiment may use the same reference numeral but with 100 added to such reference numeral.

DETAILED DESCRIPTION

Figure 20:
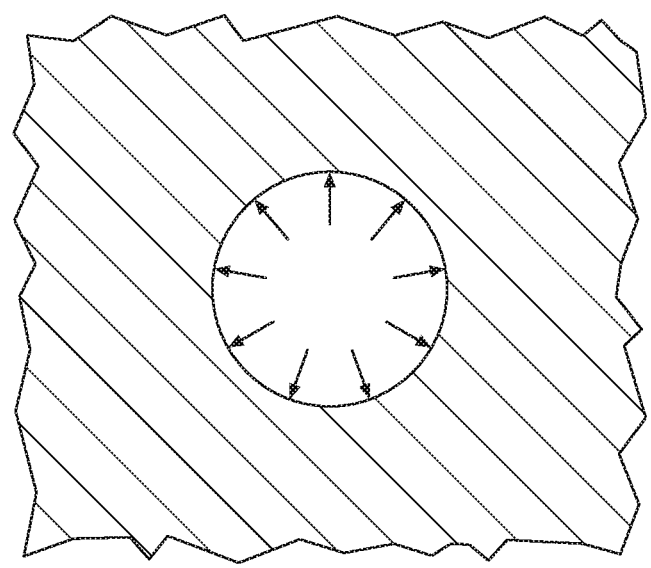
FIG. 20 depicts a cross section of the test hole shown in FIG. 19 at the crack.

Referring now to FIGS. 1-26, wherein the showings are for illustrating preferred embodiments of the present disclosure, and are not for purposes of limiting the same, the present disclosure relates to systems and methods for filling a crack 10 (see FIG. 1) in a concrete structure 12 and testing the seal effectiveness of a filling substance 22 (see FIGS. 16, 18, 20) used to fill the crack 10. Generally, there may be provided a method that may include forming a drill hole 16 and a test hole 18 in the concrete structure 12, such that both the drill hole 16 and the test hole 18 may extend into the crack 10 in spaced relation to each other. A baseline flow test may be conducted by directing a test liquid 20 (e.g., water) into the test hole 18 to determine at least one baseline liquid flow characteristic (e.g., pressure, flow rate). After the baseline flow test, the filling substance 22 may be injected into the drill hole 16 and into the crack 10 to at least partially fill a length of the crack 10 near the drill hole 16. Following hardening of the filling substance 22 in the crack 10, a quality flow test may be conducted by directing the test liquid 20 into the test hole 18 to determine at least one quality liquid flow characteristic. The baseline liquid flow characteristic may be compared to the quality liquid flow characteristic to determine an effectiveness of the injection. For instance, the baseline flow test may reveal a high flow rate and low pressure, indicative of the crack 10 not being filled. Conversely, the quality flow test may show low flow rate and high pressure, indicative of the crack 10 being suitably filled by the filling substance 22. If the quality flow test shows a high flow rate and low pressure, that may be an indication that the crack 10 may not be suitably filled.

Figure 27:
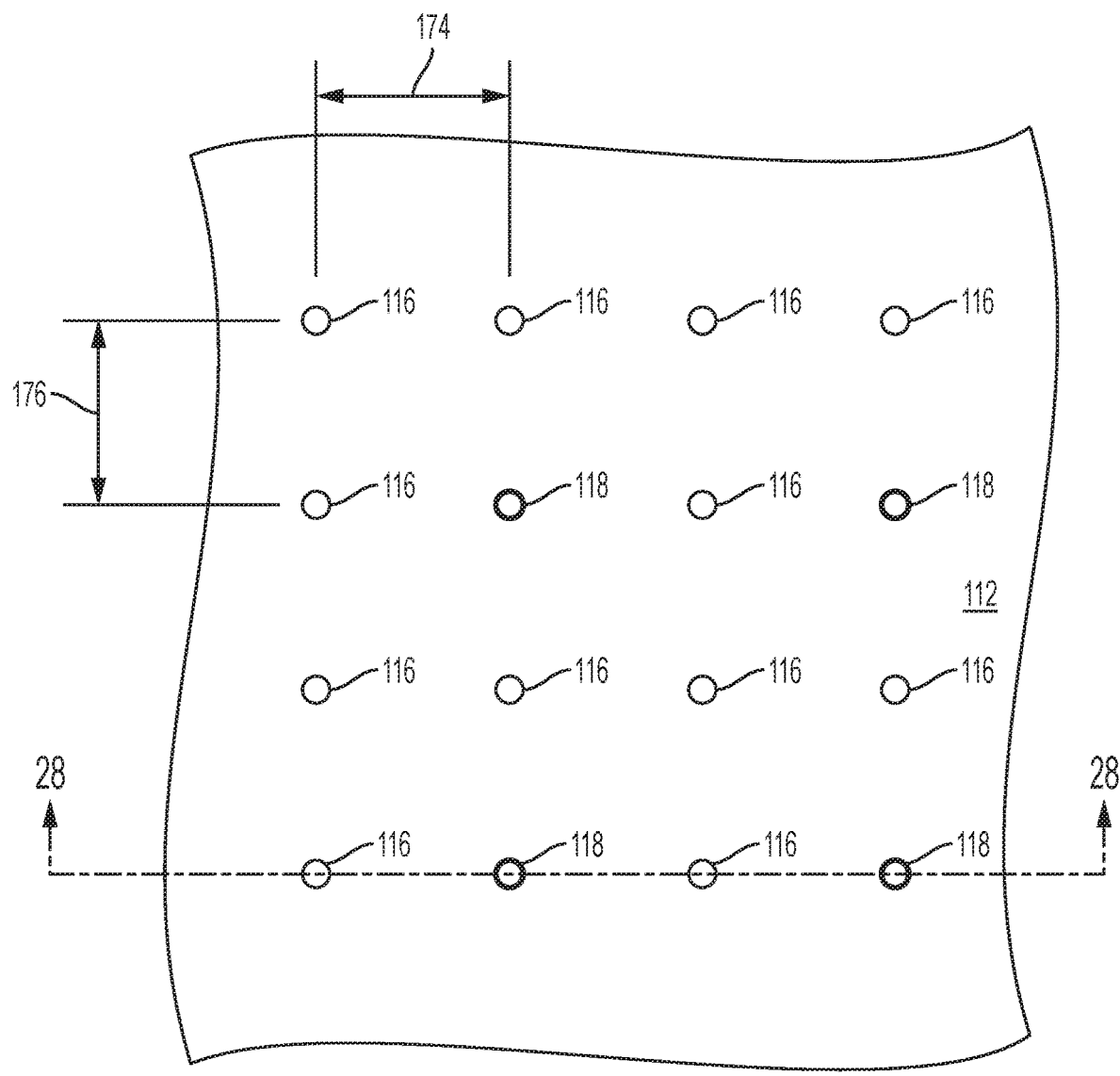
FIG. 27 illustrates a porous concrete structure.
Figure 28:
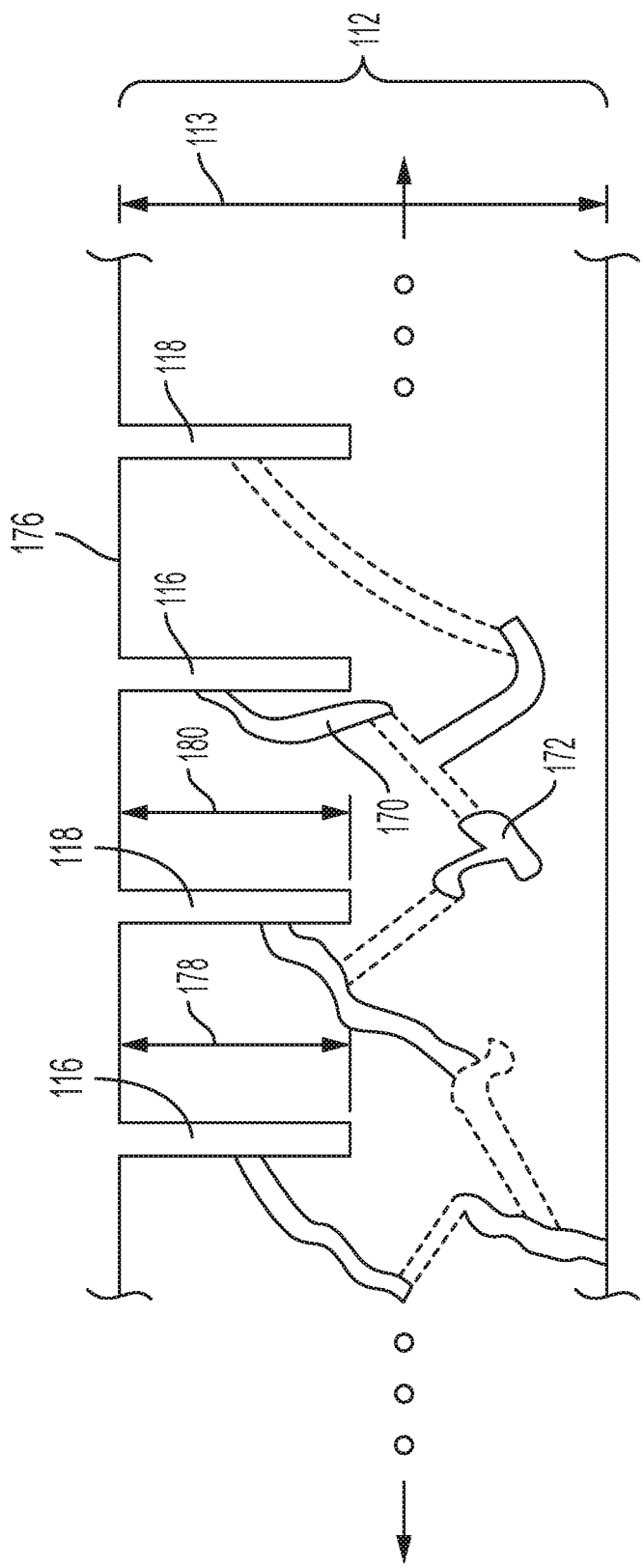
FIG. 28 is a cross sectional view of the porous concrete structure shown in FIG. 27.

Moreover, referring now to FIGS. 27 and 28, the present disclosure also relates to systems and methods for testing permeability or porosity of a substrate 112. The systems and methods may be used to test the seal effectiveness of the sealing method or to compare the porosity of different substrates to one another.

For example, the systems and methods discussed herein may be used to determine whether sealing a porous substrate (e.g., shotcrete) was effective. In particular, the substrate 112 may be formed. After forming the substrate, a pattern of test holes 118 may be formed in the structure 1112. The permeability of the substrate 112 is determined. Thereafter, the substrate may be sealed, and the permeability of the substrate is determined again to see if the sealing method was effective. Alternatively, the systems and methods described herein may be used to determine the relative permeability or porosity of the different substrates. In this regard, the systems and methods discussed herein may be used to rank the permeability or porosity of the different substrates.

When determining whether a sealing method was effective, a baseline flow test may be conducted by injecting a test liquid 20 into a plurality of test holes 18 formed in the substrate 112. This step determines at least one baseline liquid flow characteristic (e.g., flow rate or flow rate as a function of pressure). After the baseline flow test, the filling substance may be injected into a plurality of drill holes 16 and allowed to permeate throughout the entire substrate 112 so as to fill channels 170 and voids 172 in the substrate 112. Before the filling step, the test holes 18 near the current active fill hole 16 may be plugged so that the filling substance 122 does not enter the test hole 18 during the filling step. After the filling substance 200 has hardened or set, a quality flow test may be conducted by directing the test liquid into the test hole to determine at least one quality liquid flow characteristic which may be compared to the baseline liquid flow characteristic. The baseline liquid flow characteristic may be compared to the quality liquid flow characteristic to determine the effectiveness of the injection step. In general, a filling step or injecting step is effective if the ratio between flow and pressure increases before and after the filling or injecting step, as discussed in relation to FIGS. 23-26. The embodiment disclosed in relation to FIGS. 27 and 28 use all of the same aspects described in relation to FIGS. 1-26, but only the additions or modifications are shown and described below in relation to FIGS. 27 and 28.

The systems and methods discussed herein may also be used to test the relative porosities or permeabilities of different structures or different locations of one structure. These different structures may have been treated with different sealing methods. The testing device and method can determine relatively which structure is more or less porous or permeable.

The structure 12, 112 may include poured concrete, shotcrete, brick filled with concrete and any other concrete structure or porous substrate. The porous substrate may be something other than concrete including but not limited to plastic, sand, rock, et cetera.

Figure 1:
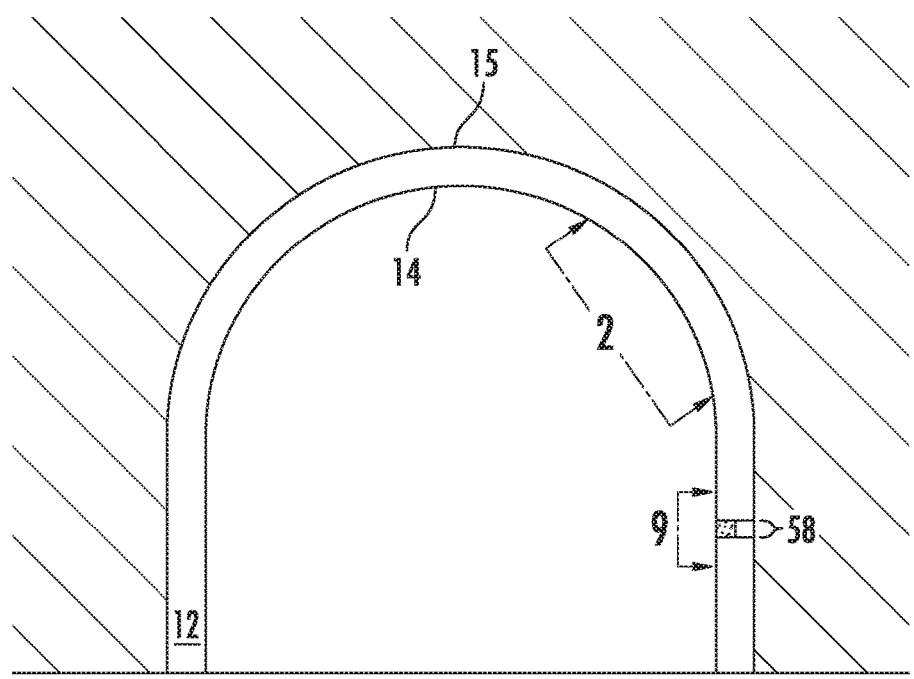
FIG. 1 is a front view of a concrete tunnel.
Figure 2:
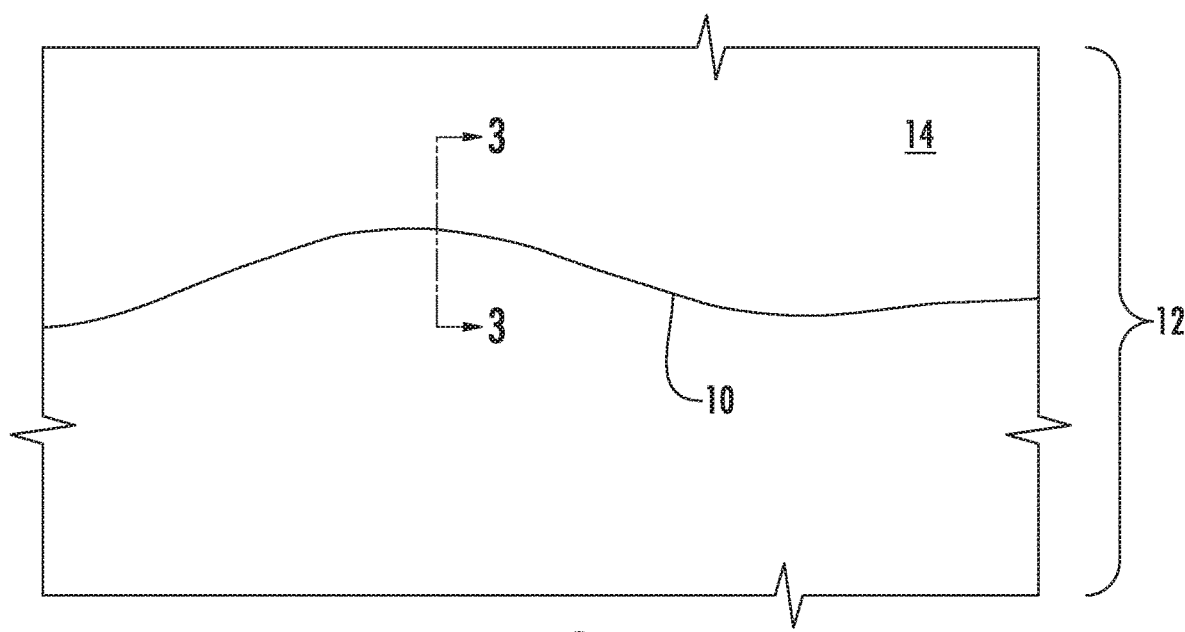
FIG. 2 is a plan view of a first surface of the tunnel having a crack formed thereon.
Figure 3:
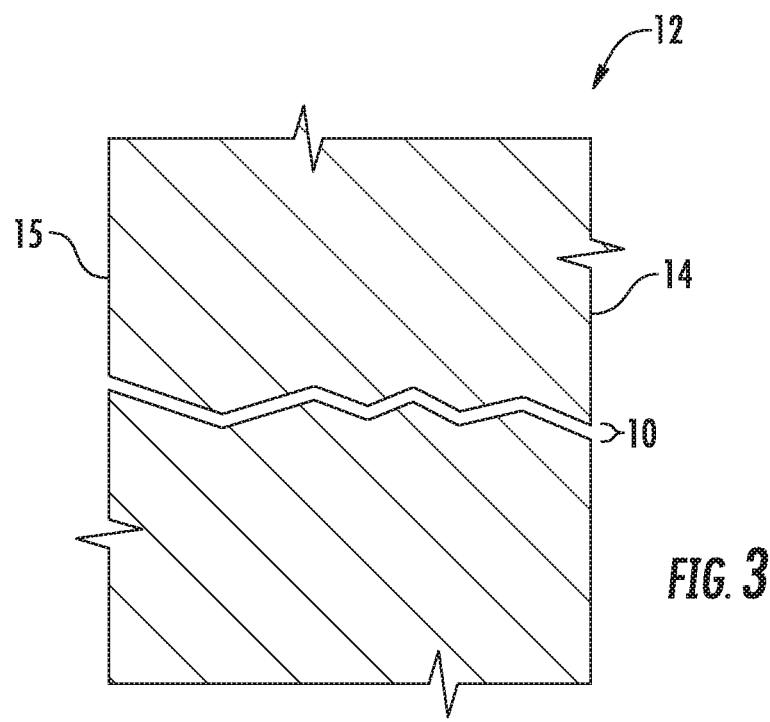
FIG. 3 is a cross section view of the crack shown in FIG. 2.

FIG. 1 shows a concrete structure 12, specifically a tunnel, having a first surface 14 positioned away from a stratum layer made up of geological elements such as rocks and soil, and a second surface 15 opposite the first surface 14 and positioned adjacent to the stratum layer. As used herein, the term concrete structure broadly refers to other structures where cracks may occur, and which may be formed of concrete or similar substances, such as brick, rock, or the like. Other concrete structures 12 may include parking structures, elevator pits, etc. FIG. 2 shows a portion of the first surface 14 where a crack 10 has formed in the concrete structure 12. The crack 10 shown is solely an exemplary leak source, and the current disclosure may also be applied to other types of cracks where water may leak in concrete structures 12, such as a joint 58 between two concrete slabs that are used in building the concrete structure 12 or precast segment joints. The crack 10 may be thick enough to allow passage of water. The leak may be caused by water from a rain event, overhead plant watering, or hydrostatic ground water pressure. FIG. 3 shows a portion of the cross section of the crack 10 extending from the second surface 15 to the first surface 14, where water may travel from the second surface 15 (see FIG. 1) to the first surface 14 (see FIG. 1).

Figure 4:
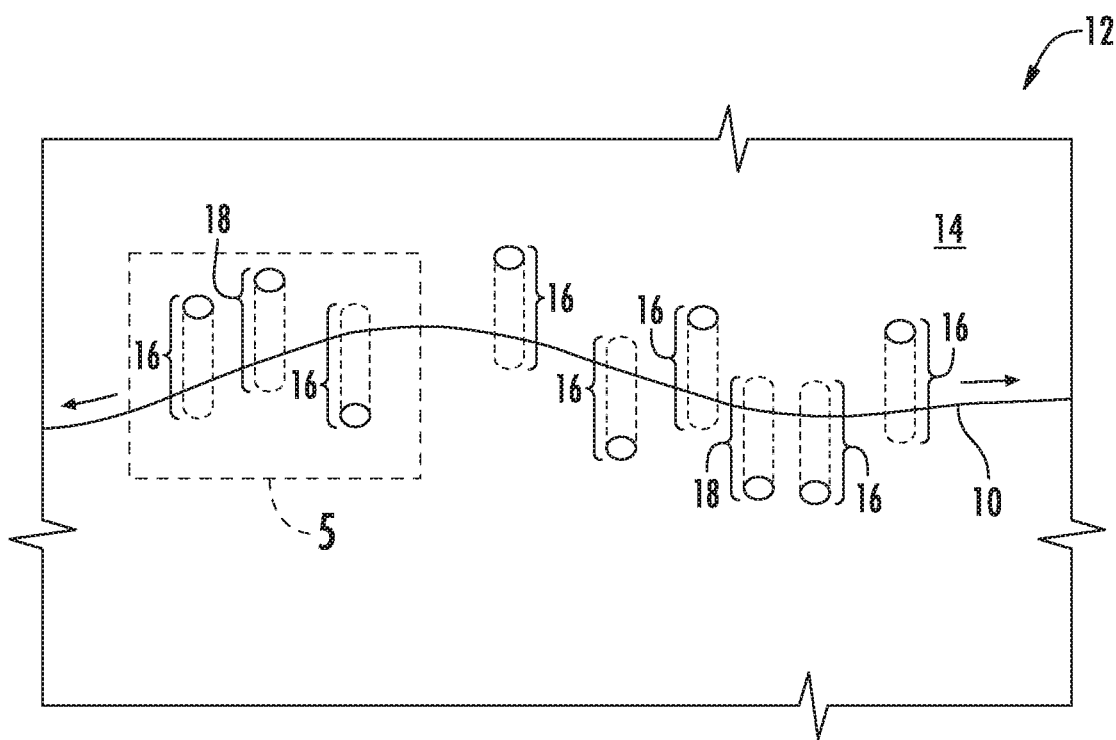
FIG. 4 is a plan view of the first surface of the tunnel shown in FIG. 2 with drill holes and test holes drilled along the crack.

The method of filling the crack may include forming drill holes 16 and test holes 18 along the crack 10. FIG. 4 shows drill holes 16 and test holes 18 along the lateral crack 10 propagation extending from the first surface 14 into the concrete structure 12. The depth of the drill holes 16 and test holes 18 may exceed the depth of the crack 10 from the first surface 14. Preferably, the drill holes 16 and test holes 18 penetrate the first surface 14 at a 45-degree angle and penetrate the crack 10 so that the holes 16, 18 are on both sides of the crack 10. The drill holes 16 may have a diameter between 0.2 inches and 3 inches, and more preferably between 0.2 inches to 1 inch, and even more preferably 0.5 inches. The drill holes 16 may be spaced 6 inches to 18 inches, and more preferably 12 inches, apart by a distance. Likewise, the test holes 18 may have a diameter between 0.2 inches and 3 inches, preferably 0.5 inches, and may be drilled at a location within 3-inch to 7 feet depending on the type of substrate, preferably 12-inch, space between two drill holes 16. These measurements may be proportional to crack 10 dimensions, meaning they may increase or decrease with crack 10 size. A drill capable of drilling a 0.5-inch hole into concrete may be used to drill the drill holes 16 and test holes 18. The drill holes 16 and test holes 18 may be drilled at an angle between 20 degrees to 60 degrees, preferably 45 degrees to a plane parallel or tangent to the first surface 14. However, the drill angle may be between 60 degrees and 90 degrees. For example, in thin substrates, the angle may be perpendicular or 90 degrees. A drill hole 18 may also be drilled on the opposite side of the crack 10 relative to a drilled drill hole 18. Adjacent drill holes 16 may be drilled in opposite directions of each other. A test hole 18 may be drilled in the same direction as the drill hole 16 the test hole 18 is being used to test. The drill holes 16 and test holes 18 may be flushed out with water after drilling and prior to use.

Figure 5:
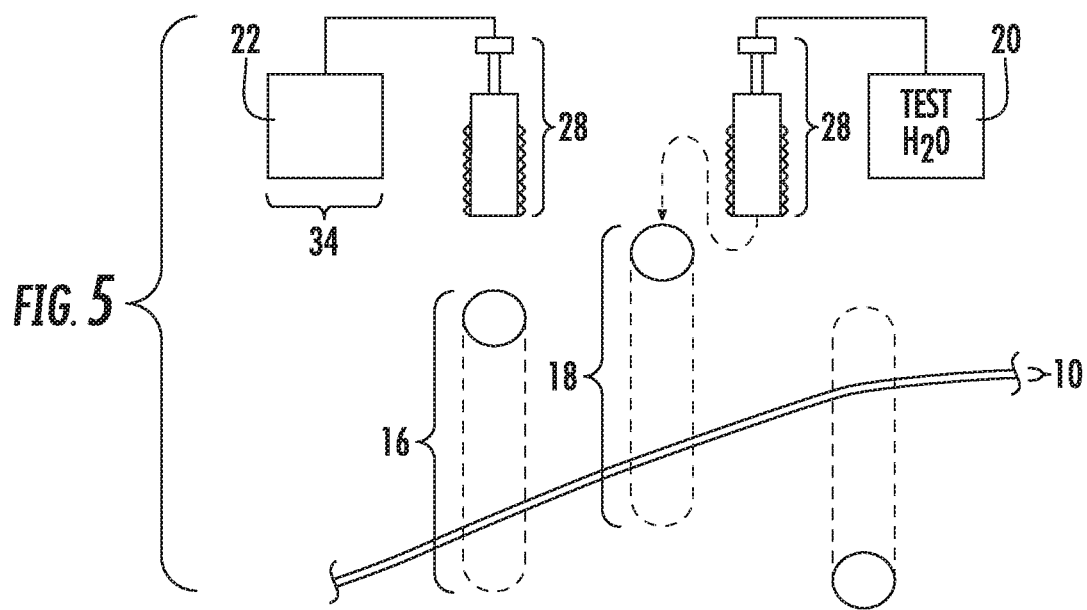
FIG. 5 is an enlarged view of the drill hole and test hole shown in FIG. 4 undergoing a baseline flow test.

FIG. 5 shows a preparation for directing a test liquid 20 or a test gas into a test hole 18 to conduct a baseline flow test. A baseline flow test may involve inserting a mechanical packer 28 into the test hole 18, pumping a test liquid 20 into the test hole 18 through the mechanical packer 28 at constant pressure, and taking readings of one or more baseline liquid flow characteristic data with testing equipment (shown in FIGS. 21 and 22). Preferably, the baseline flow test should be conducted at most significant water flow areas first and then moved to areas with less flow. Determining the magnitude of water flow in an area may simply require a visual inspection of the leak.

The mechanical packer 28 may generally be defined by a top, bottom, shaft, and rubber base. The diameter of the rubber base may correspond to the dimensions of the counterpart hole 16 or 18. As such, the diameter of the rubber base may be between 0.2 inches and 3 inches, preferably 0.5 inches, to fill the 0.2-inch to 3-inch, preferably 0.1 inch to 1 inch, and more preferably 0.5-inch, test hole 18. The length of the mechanical packer 28, measured from top to bottom, may be between 1 inch and 20 inches, and more preferably 4 inches. The mechanical packer 28 may be steel, aluminum, brass, zinc, or other metal alloys used in manufacturing packers for the concrete repair industry. A steel mechanical packer 28 may be preferred due to its high pressure tolerance and resistance to oxidation. However, an aluminum mechanical packer 28 may be an alternative option due to its economical pricing and relatively high pressure tolerance. An exemplary mechanical packer 28 may be ACP-2011, which is supplied by Alchemy Spetec.

As shown in FIG. 5, the test liquid 20 may be water. The testing equipment may draw water 20 from a water source 32 and the volume of water required may depend on the dimensions of the crack 10. The water may be drawn via an inlet hose 29 (shown in FIGS. 21 and 22). The inlet hose 29 may be a nylon tube or any other similar material to have a similar resistance to fatigue and fracture. The drawn water 20 may pass through a pump 46 of the testing equipment that directs water 20 to the mechanical packer 28 via an outlet hose 30 at a constant pressure. The water 20 pressure may be at least 10 psi and is preferably between 300 psi, and more preferably 150 psi. The outlet hose 30 may be a material sufficient to withstand the pressure rating of the water pump 46.

The baseline flow test may produce at least one baseline flow characteristic, and more preferably multiple baseline flow characteristics, such as baseline pressure and baseline flow rate. A low baseline flow pressure and a high baseline flow rate may be observed due to the drill hole 16, the crack 10, and the test hole 18 having not yet been filled with the filling substance 22. The pressure and flow rate may be measured by the testing equipment as the water travels from the mechanical packer 28 that is inside the test hole 18 into the crack 10 and exits through the second surface 15. The pressure may be measured in psi and the flow rate may be measured in milliliters per minute (mL/min) since they are the industry standard units. However, the pressure and flow rate may ultimately be measured in any metric and English unit of pressure and flow rate, respectively. The pressure and flow rate may be collected via a pressure meter 48 and flow meter 50, respectively. The pressure meter 48 and the flow meter 50 may be connected to the water line with water-tight T-fittings after water exits the pump 46. The pressure meter 48 and flow meter 50 may measure data to be recorded at a specified time interval set by the user. The preferable time interval may be 1 second to 2 minutes, and more preferably 30 seconds. A programmable logic controller ("PLC") may be in communication with the pressure meter 48 and flow meter 50 and receive real time pressure and flow readings. The PLC may be in communication with a human machine interface ("HMI") 52 and display the readings. The PLC may further generate a data set computed by dividing the flow rate ("Q") by the pressure ("P") at a certain time, which may be referred to as the "QP Factor." A unique location number may be assigned to each test hole 18 via the HMI 52 to distinguish the data of each test hole 18 recording. Additionally, the number of readings to be taken and recorded may be set via the HMI 52. Following the completion of data collection, the recorded data may be saved on a Universal Serial Bus ("USB") drive by inserting the USB drive into a USB port 40 that is in communication with the PLC. Preferably, the data may be collected at the end of each testing day.

Figure 6:
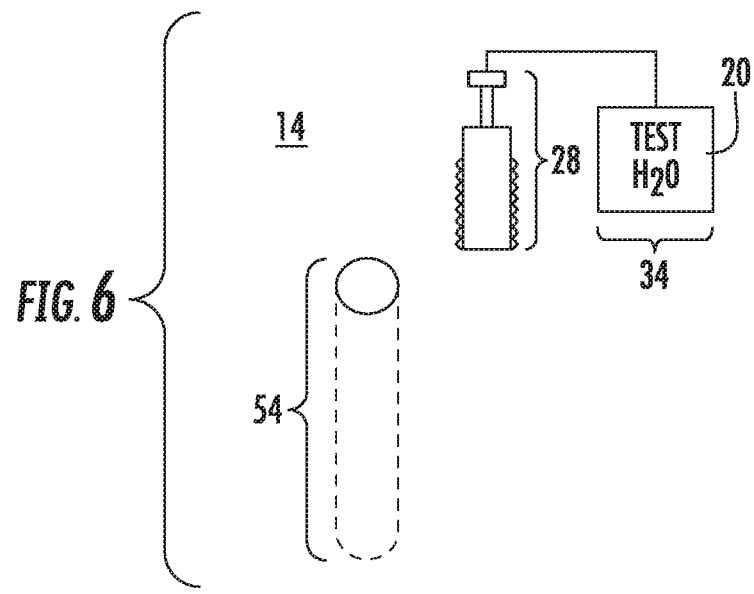
FIG. 6 is a schematic view of a dead hole undergoing a baseline flow test.

Referring to FIG. 6, a second embodiment of a baseline flow test may include injecting a test liquid 20 inside a hole 54 drilled into concrete where no crack 10 or joint 58 is present and taking pressure and flow measurements of the test liquid 20. The hole 54 may be referred to as a "dead hole." A dead hole 54 may mimic a test hole 18 at least partially filled with filling substance 22. Conducting a baseline flow test at the dead hole 54 and interpreting how similar the data of a quality flow test that follows is to that of the baseline flow test may indicate the effectiveness of the crack 10 filling procedure. Preferably, the dead hole 54 may have a 0.2-inch to 3-inch, and more preferably 0.5-inch diameter. The dead hole 54 may be drilled from the first surface 14 using a drilling tool capable of drilling a hole with the dimensions mentioned here. The dead hole 54 may have a depth that reaches halfway between the first surface 14 and second surface 15. The testing equipment may draw a test liquid 20, which may be water, from a source 32 and the volume of test liquid 20 required may depend on the dimensions of the dead hole 54. The test liquid 20 may be drawn and directed into the dead hole 54 via a mechanical packer 28 as described above. The pressure and flow rate may be measured and recorded by the testing equipment as the test liquid 20 travels from the mechanical packer 28 into the dead hole 54 as described above. Following the filling procedure at the drill hole 16 and conducting a quality flow test for the drill hole 16, the baseline flow test data and the quality test data, which may include pressure and flow rate, may be compared to interpret the effectiveness of the filling based on the pressure and flow rate similarity between the two tests.

Figure 7:
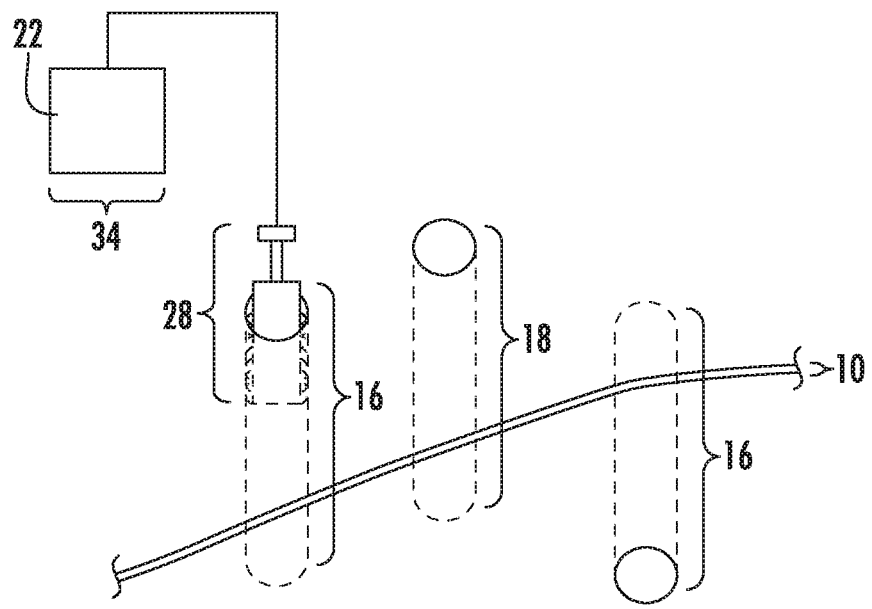
FIG. 7 is a plan view of a drill hole being injected with a filling substance.

After conducting the baseline flow test and recording the data, the mechanical packer 28 inside the test hole 18 may be removed, and a new mechanical packer 28 may be inserted into a drill hole 16 to inject a filling substance 22 into the crack 10, as shown in FIG. 7. The mechanical packer 28 may have the same specifications as those of the mechanical packer 28 described above. Once inside the drill hole 16, the mechanical packer 28 exterior may be flushed against the drill hole 16 surface. The filling substance 22 may be drawn from a filling substance source 34 and pumped into the drill hole 16 via a high pressure pump. The filling substance 22 may be a chemical grout including solutions of two or more chemicals that react to form a gel or foam product (e.g., a solid precipitate). There is a wide range of chemical grouts available for use in the industry (e.g., polyurethane resin, epoxy resin, polyurea resin, ultrafine cement grout). Considerations for selecting a chemical grout may include crack width, crack movement, amount of infiltration, method of injection, and jobsite conditions. The filling substance 22 may be filled in from a particular drill hole 16 until the filling substance 22 is observed at an adjacent drill hole 16. This signifies the filling substance 22 being filled in the crack 10 itself. The filling substance 22 may also partially or completely fill the adjacent test hole 18. The filling substance 22 may harden at a rate based on the properties of the chosen chemical grout.

Figure 8:
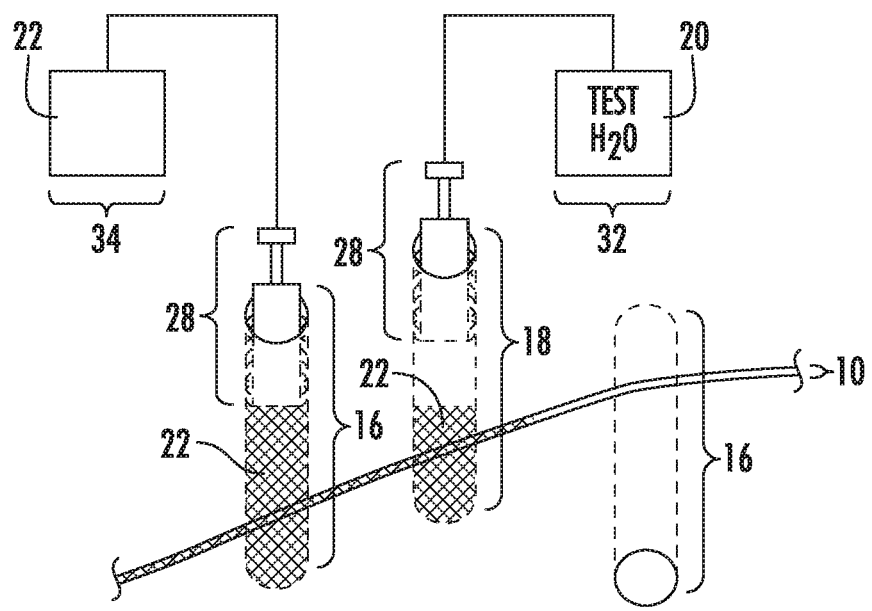
FIG. 8 depicts a filled drill hole and a test hole undergoing a quality flow test.
Figure 9:
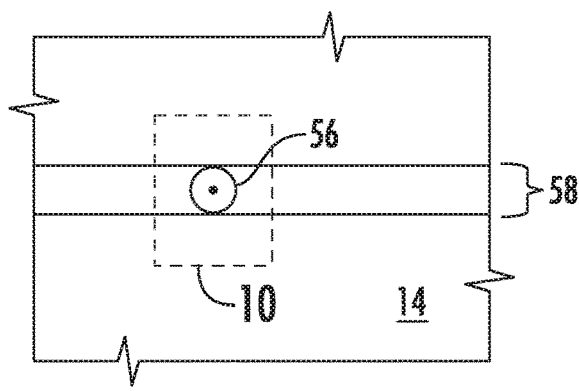
FIG. 9 is an enlarged view of the joint with the injection tube system shown in FIG. 1.
Figure 10:
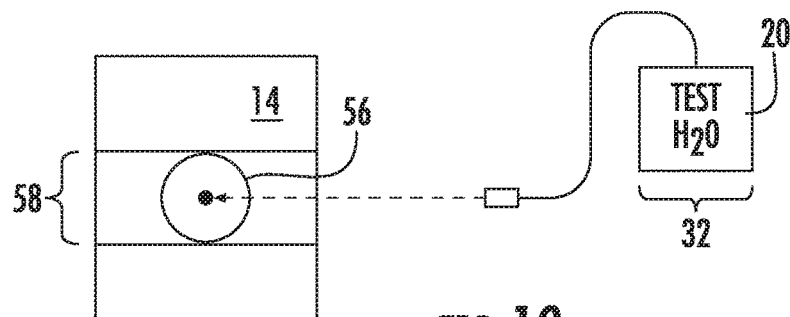
FIG. 10 is an enlarged view of the joint with the injection tube system undergoing a baseline flow test.
Figure 11:
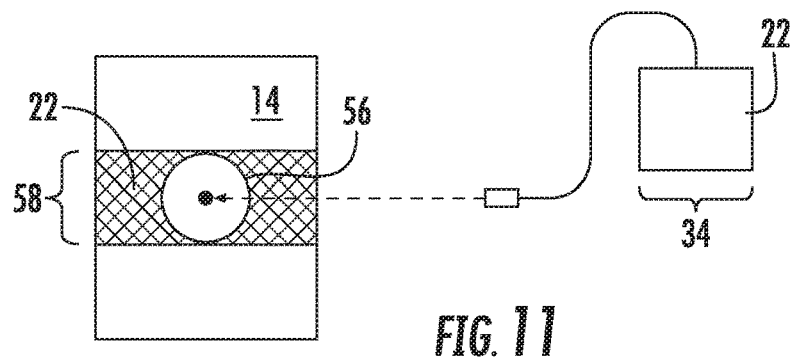
FIG. 11 is an enlarged view of the joint with the injection tube system being injected with a filling substance.
Figure 12:
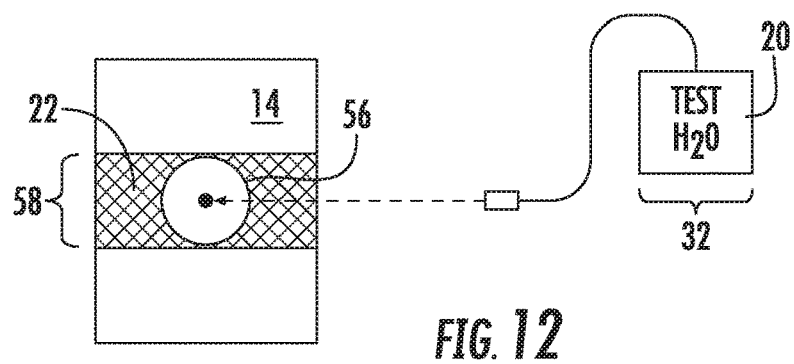
FIG. 12 is an enlarged view of the joint with the injection tube system undergoing a quality flow test.

Following the injection and hardening of the filling substance 22, a quality flow test may be conducted to compare the test results to that of the baseline flow test, as shown in FIG. 8. A high-quality flow pressure and a low-quality flow rate may be observed due to the drill hole 16, the crack 10, and the test hole 18 having been filled with the filling substance 22. Like the baseline flow test, a quality flow test may involve inserting a mechanical packer 28 into the same test hole 18, pumping a test liquid 20 into the test hole 18 through the mechanical packer 28 at constant pressure (e.g., 150 psi), and taking readings of one or more liquid flow characteristic data with testing equipment. The steps taken in conducting the quality flow test, the type of data collected, and the method of recording data are the same as those of the baseline flow test mentioned above. After the quality flow test is conducted for a particular drill hole 16 and test hole 18 pair and the data has been recorded, the procedures discussed above may be repeated for an adjacent drill hole 16 and test hole 18 pair, starting with a new baseline flow test. Alternatively, some or all drill holes 16 may be filled simultaneously and a quality flow test for each filled drill hole 16 may be conducted at the same time using multiple testing equipment.

The methods mentioned above may be further modified to be compatible with injection tubes 56, as shown in FIGS. 9-12. Injection tubes 56 allow injection of cold and construction joints 58 via a pre-installed injection canal. An injection tube 56 may be placed in a joint 58 during construction and may act as a canal for the filling substance 22, which will, when in contact with water, expand and seal the joint 58 permanently. The baseline flow test mentioned above may be conducted for an injection tube 56 by connecting the supply outlet 30 to the injection tube 56, injecting a test liquid 20 into the injection tube 56, and collecting data for a specified time (e.g. 1 minute). The location number of each injection tube 56 may be notated via the HMI 52 to distinguish the collected data. Next, the filling substance 22 may be injected via the injection tubes 56. The filling substance 22 may be an acrylic chemical grout or other flushable filling substance. The filling substance 22 and the filling process of the injection tubes 56 may vary across the industry. Prior to the hardening of the filling substance 22, the injection tubes 56 may be flushed with water to ensure the injection tube 56 channel stays open for further testing and filling injections. Following the hardening of the filling substance 22, the quality flow test mentioned above may be conducted for the injection tubes 56 by repeating the previously discussed steps of the baseline flow test for the injection tubes 56. The data from both tests may be displayed on the HMI 52, saved on a USB drive, and graphed via a graphing software for comparison to determine the effectiveness of the injection tube 56 filling.

Figure 13:
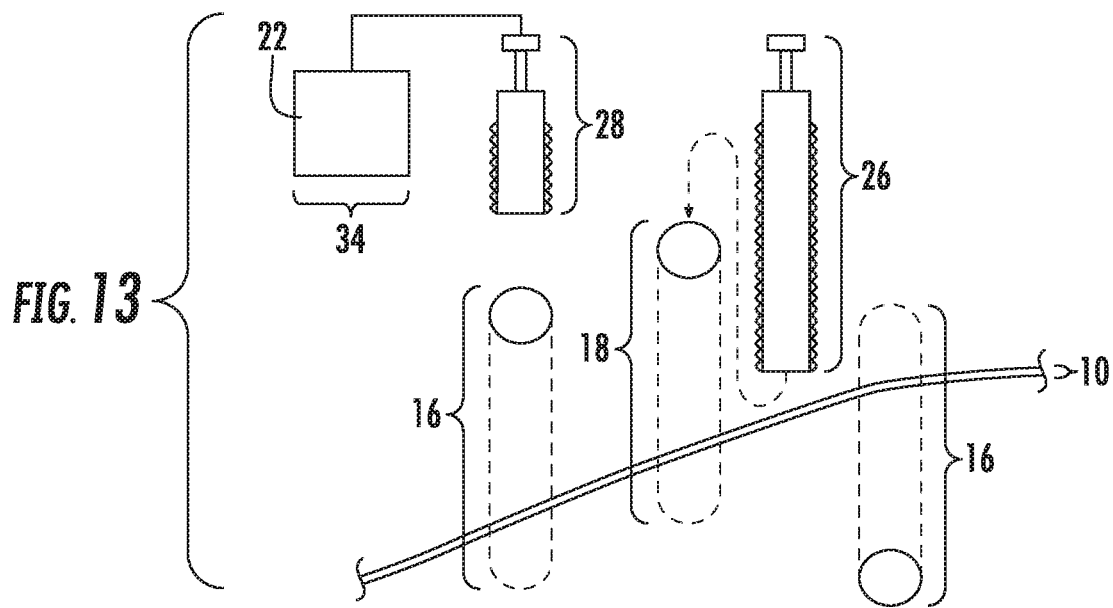
FIG. 13 depicts a drill hole and a test hole with a plug being inserted into it.
Figure 14:
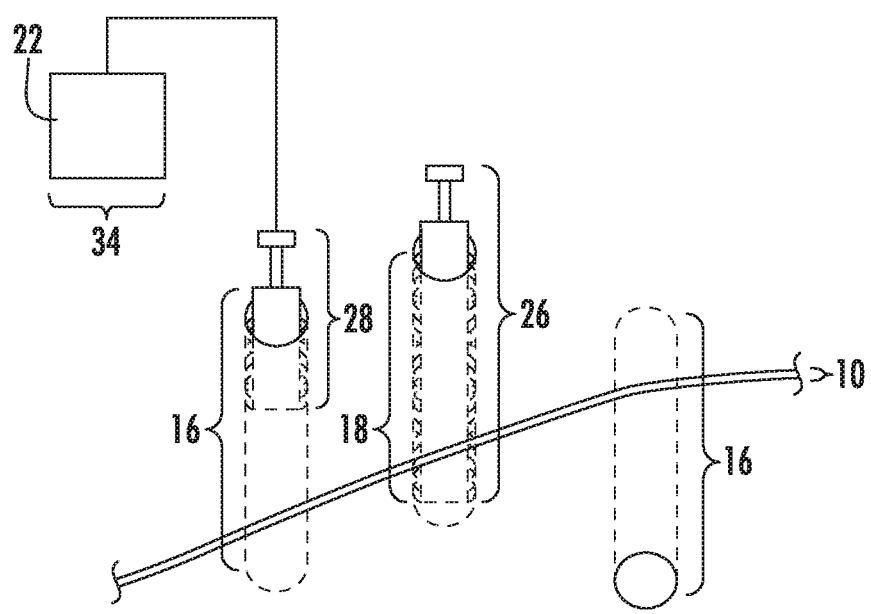
FIG. 14 depicts a mechanical packer for packing filling substance inserted into the drill hole shown in FIG. 13 and the test hole shown in FIG. 13 with the plug fully inserted.
Figure 15:
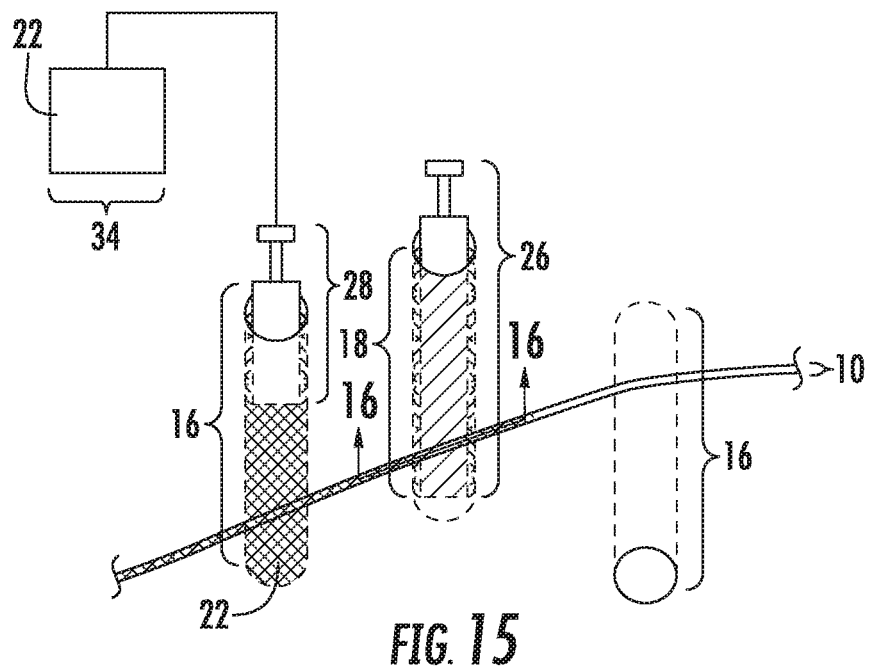
FIG. 15 depicts the drill hole shown in FIG. 13 being filled with a filling substance while the test hole shown in FIG. 13 is plugged.
Figure 16:
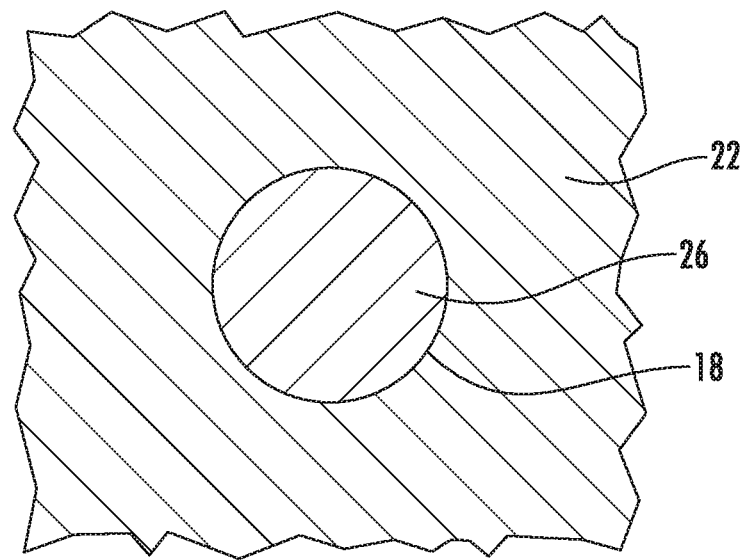
FIG. 16 depicts a cross section of the test hole shown in FIG. 15 at the crack.
Figure 17:
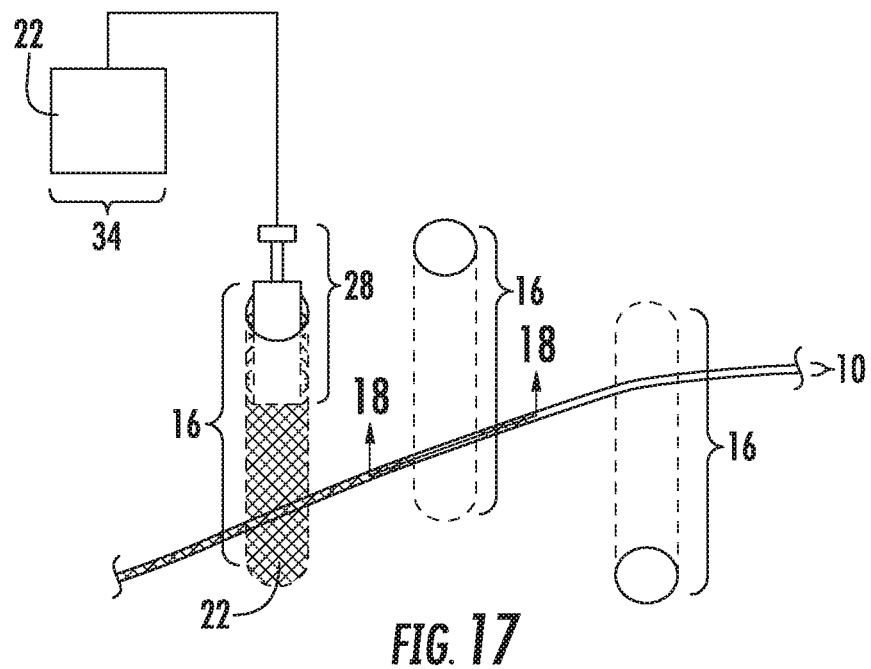
FIG. 17 depicts the plug of the plugged test hole shown in FIG. 15 being removed.
Figure 18:
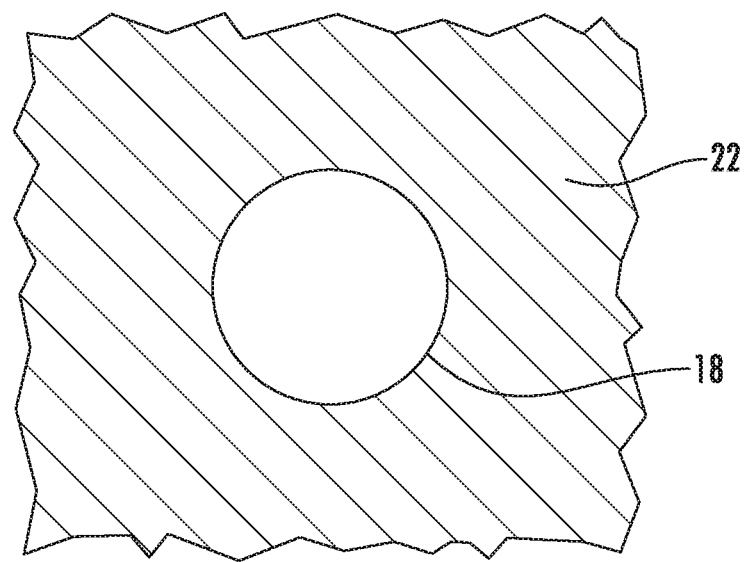
FIG. 18 depicts a cross section of the test hole shown in FIG. 17 at the crack.
Figure 19:
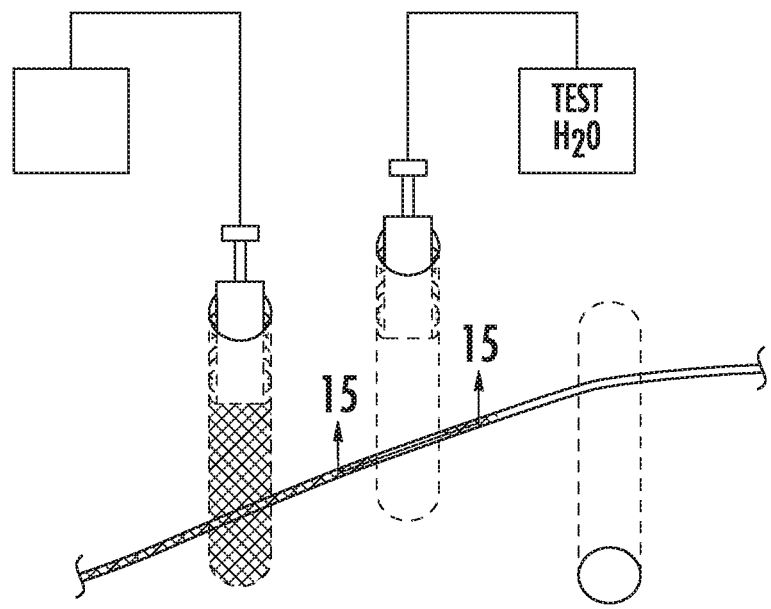
FIG. 19 depicts the drill hole and the test hole shown in FIG. 17 undergoing a quality flow test.

FIGS. 13-20 show another variation of the aforementioned method of injecting a filling substance 22 into the crack 10 and conducting a quality flow test. In this embodiment, a plug 26 may be inserted into the test hole 18, as shown in FIG. 13. When the filling substance 22 is injected from the drill hole 16, the plug 26 may prevent the filling substance 22 from entering the test hole 18. When the plug 26 is removed, the test hole 18 is empty with no filling substance 22. The filling substance 22 may be hardened around the plug 26 at the crack 10 rather than allowing the filling substance 22 to reach inside the test hole 18 when filling the drill hole 16. The quality flow test data collected, namely the quality flow pressure and flow rate, from the test liquid 18 traveling further down the test hole 18 into the crack 10 may provide a better understanding of how effective the filling procedure was. The plug 26 may have a 0.2-inch to 3-inch, preferably 0.2 inch to 1 inch and more preferably 0.5-inch, diameter and have an exterior that is flushed against the test hole 18, which may have a 0.2-inch to 3-inch, preferably 0.5-inch, diameter. The plug 26 may be complementary in shape to the test hole 18 and long enough to, at least partially, and more preferably completely intersect the crack 10. Next, the filling substance 22 may be injected into the drill hole 16 and the crack 10 with the plug 26 inserted, as shown in FIG. 14. FIG. 15 shows the filling substance 22 filling the drill hole 16 up to and around the mechanical packer 28 and the crack 10 partially, wherein the filling substance 22 circumvents the plug 26. FIG. 16 shows a cross section of the plug 26 inside the test hole 18 and the filling substance 22 surrounding it. Once the filling substance 22 hardens, the plug 26 may be removed from the test hole 18. FIG. 17 shows the hardened filling substance 22 filling the drill hole 16 up to the mechanical packer 28 and the crack 10 partially, wherein the hardened filling substance 22 surrounds the perimeter space of the plug 26. FIG. 18 shows a cross section of the test hole 18 at the crack 10 and the filling substance 22 surrounding it without the plug 26. Next, a quality flow test may be conducted by inserting a mechanical packer 28 into the test hole 18, pumping a test liquid 20 into the test hole 18 through the mechanical packer 28 at constant pressure (e.g., 150 psi) (see FIG. 19), and taking readings of one or more liquid flow characteristic data with testing equipment (e.g., pressure and flow rate). The steps taken in conducting the quality flow test, the type of data collected, and the method of recording data are the same as those of the baseline flow test mentioned above. A high-quality flow pressure and a low-quality flow rate may be observed due to the drill hole 16 and the crack 10 having been filled with the filling substance 22. However, the quality flow pressure maybe lower and the quality flow rate may be higher than those resulting from a quality flow test with a filled test hole 18. As better illustrated in the cross-section depiction of FIG. 20, the flow of test liquid 20 may be obstructed by the hardened filling substance 22 surrounding the test hole 18 at the crack 10, and a back pressure may be observed.

Figure 21:
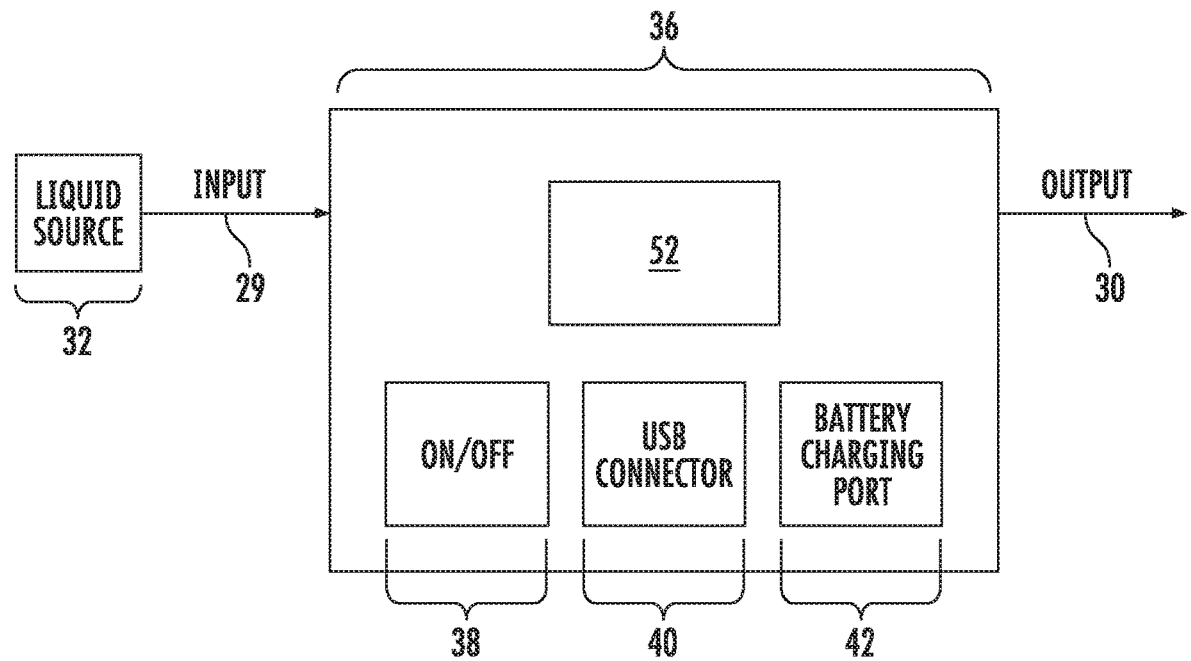
FIG. 21 is a schematic view of the components of the testing equipment.

FIG. 21 shows a schematic diagram of the testing equipment used in both baseline and quality flow tests. The components of the testing equipment may be contained in a case 36. The case 36 may be waterproof. The case 36 may include an on/off switch 38. The on/off switch 38 may be in electronic communication with the PLC and the battery 44 and may turn on/off the HMI 52 when pressed. The case may further include a USB connector 40. A USB drive may be connected to the USB connector 40, which may be in electronic communication with the PLC, and testing data may be transferred from the PLC onto the USB drive. The case may further include a battery charging port 42. A charging cord may be connected to the charging port 42 and may transmit power from a power source to charge the battery 44 within the case 36. The case 36 may be connected to an inlet line 29 and an outlet line 30, which may be hoses manufactured from a pressure resistant material known in the industry, such as nylon.

Figure 22:
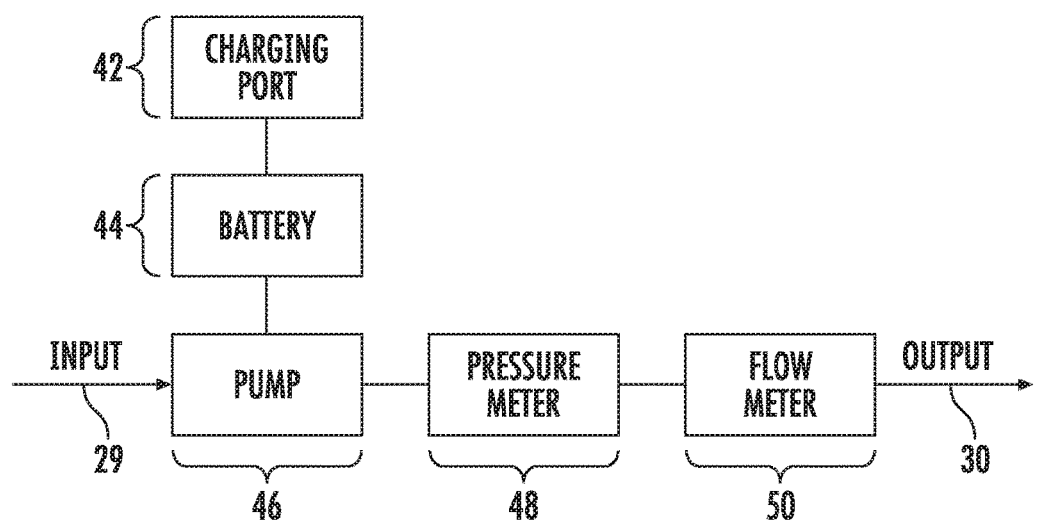
FIG. 22 is a schematic view of the test liquid flow and the electrical connections between the components of the testing equipment.

As shown in FIG. 22, which is a schematic illustration of electrical and fluid related components of the testing equipment, the inlet line 29 may direct a test liquid 20 into the pump 46. The pump 46 may be turned on/off from the HMI 52, which may be in electronic communication with the PLC, which may be connected to a relay switch that may open and close the circuit that may power the pump 46. communication with the PLC. The pump 46 may be powered by the battery 44. The pump 46 may direct the test liquid 20 into the pressure meter 48 and the flow meter 50, both of which may be in electronic communication with the PLC. The pressure meter 48 and the flow meter 50 may deliver real-time readings to the PLC, which may be displayed on the HMI 52. After passing through the pressure meter 48 and the flow meter 50, the test liquid 20 may exit the case 36 via the supply outlet 30, which may direct the test liquid 20 to the mechanical packer 28 to ultimately travel into the test hole 18.

The collected data from the baseline and quality flow tests may be graphed against time for comparison. A graphing software may be used to generate the graphs and the data may be transferred to a computer in which the software runs via a USB drive. A flow rate versus time graph of baseline test results may indicate a high flow rate, such as in FIG. 23. A pressure versus time graph of baseline test results may indicate a low pressure, such as in FIG. 24. These graphs may be helpful in understanding how water behaves in the crack 10 prior the injecting the filling substance 22. In comparison, a flow rate versus time graph of quality flow test results may indicate a low flow rate, such as in FIG. 25, and a pressure versus time graph of quality flow test results may indicate a high pressure, such as in FIG. 26. When the quality flow test graphs are compared to those of the baseline test, the effectiveness of the crack 10 filling procedure may be gauged by the changes in pressure and flow rate. The relative decrease in the flow rate and increase in pressure may be a quantifiable effectiveness metric for the user. If the desired effectiveness has been achieved, the drill holes 16 may be patched. The test holes 18 may be patched or left open and marked for future testing.

Referring now to FIGS. 27 and 28, a substrate 112 is shown. The substrate 112 may be a layer of shotcrete, a column of concrete, or any type of porous substrate made from concrete or other materials. The substrate 112 may have a thickness 113 as shown in FIG. 28. FIG. 28 shows that the substrate may have a series of interconnecting channels 170 to each other and voids 172. The voids 172 are large areas (i.e., shadows in the shotcrete industry) in the substrate 112. The channels 170 and voids 172 are interconnected which cause the substrate 112 to be porous. If water is poured on one side and pressure is applied, the water will seep into the substrate 112 due to its permeability. In contrast to FIG. 2, the substrate 112 does not have a limited number of cracks as is shown and described in relation to the embodiment shown in FIG. 2. Rather, the channels 170 and voids 172 may exist throughout the entire substrate 112. For example, shotcrete may be porous. Flooring or a wall that is made from shotcrete may absorb water that is poured on top of the surface or pushed through the surface.

The following method uses the device described above in relation to FIGS. 1-26 to measure permeability of the substrate 112 as well as effectiveness of a sealing technique to reduce permeability of the substrate 112. In particular, the method may include the step of forming a pattern of fill holes 116 and test holes 118. The fill holes 116 and drill holes 118 may be spaced apart from each other by a distance 174, 176. The distance 174 laterally may be equal to the distance 176 vertically. However, it is also contemplated that the lateral and vertical distances 174, 176 may be different from each other. Preferably, the distances 174, 176 are between 12 inches 48 inches.

The plurality of test holes 118 may be formed before the plurality of fill holes 116. After drilling the test holes 118 and before drilling the fill holes, a permeability test may be performed. Thereafter, the plurality of fill hole 116 may be formed. The fill hole 116 may then be filled with a filling substance to fill in the channels 170 and voids 172. When the filling substance 122 is injected into the substrate 112 via the fill holes 116, the test holes 118 are plugged so that the filling substance does not enter the test holes 118 through the channels 170 and voids 172 that interconnect the fill holes and the test holes. After the filling step, the user may then test the permeability via the test holes 118 with a second permeability test to see if the sealing or filling step was effective.

The fill holes 116 and the test holes 118 may be drilled into the substrate 112 so that they are generally perpendicular to an exterior surface 176. The fill and test holes 116, 118 may also be generally parallel to each other, as shown in FIG. 28. In this regard, a central axis of the holes 116, 118 may be formed preferably to be within plus or minus of 15 degrees perpendicular to the exterior surface 176 and parallel to each other. Although the holes 116, 118 have these geometric relationships to each other as well as the exterior surface 176, it is also contemplated that the holes 116, 118 may be formed at skewed angles (i.e., greater than 15 degrees but less than 45 degrees) to the exterior surface 176 and with respect to each other. However, it is preferred that the holes 116, 118 have a repeating pattern throughout the substrate 112 that is evenly spread apart.

Moreover, it is also contemplated that the holes 116, 118 is preferably drilled to a depth 178, 180 which is about one-half the thickness 113 of the substrate 112. Moreover, although it is shown and described that the depths 178, 180 of the fill and test holes 116, 118 may be equal to each other, it is also contemplated that the depths 178, 180 may be different from each other. Moreover, the depth can be more than or less than one-half of the thickness 113 of the substrate 112. By way of example and not limitation, the depths 178, 180 may be one-quarter or three-fourth of the thickness 113 of the substrate 112. In general, when the holes 116, 118 have a depth 178, 180 of one-half of the substrate 113, the holes 116, 118 will hit or intersect a sufficient number of channels, 170, 172 that eventually lead to most or if not all of the other channels 170, 172. As such, if some of the channels do not fluidly connect to one of the fill holes 116 or test holes 118, the non-connecting channels 170, 172 will be connected to the other ones of the test holes and drill holes 118, 116.

Figure 23:
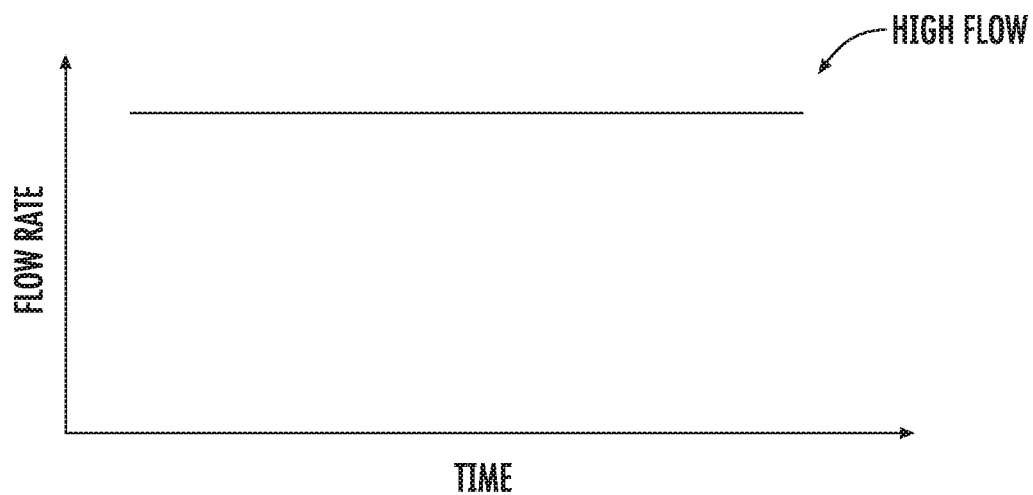
FIG. 23 is a graph of a baseline flow test flow rate data against time.
Figure 24:
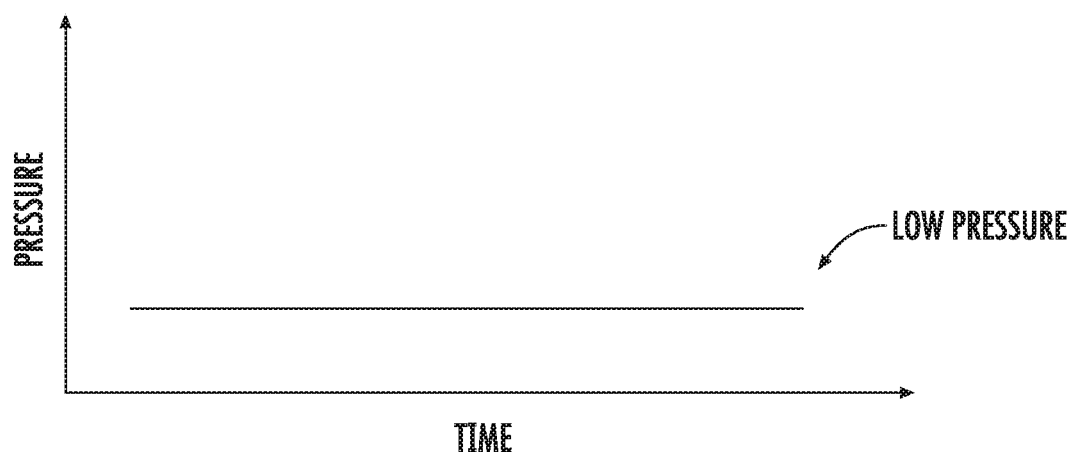
FIG. 24 is a graph of a baseline flow test pressure data against time.
Figure 25:
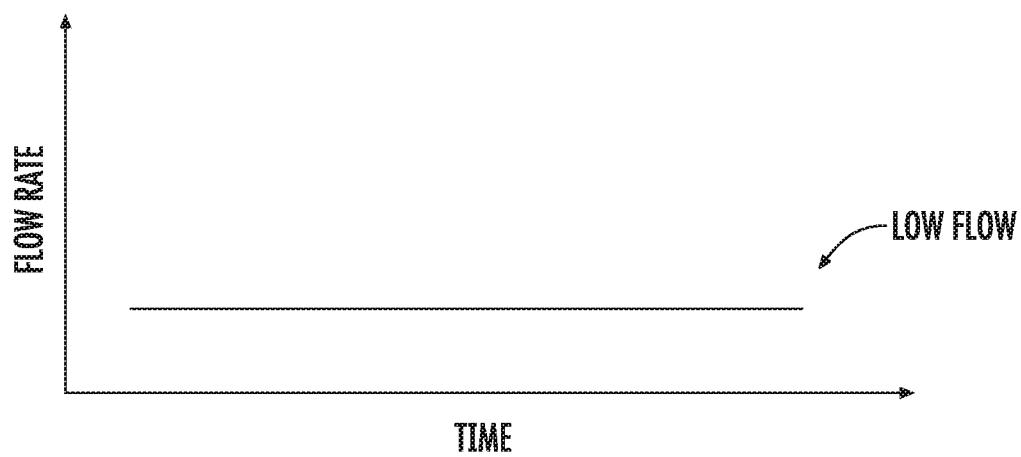
FIG. 25 is a graph of a quality flow test flow rate data against time.
Figure 26:
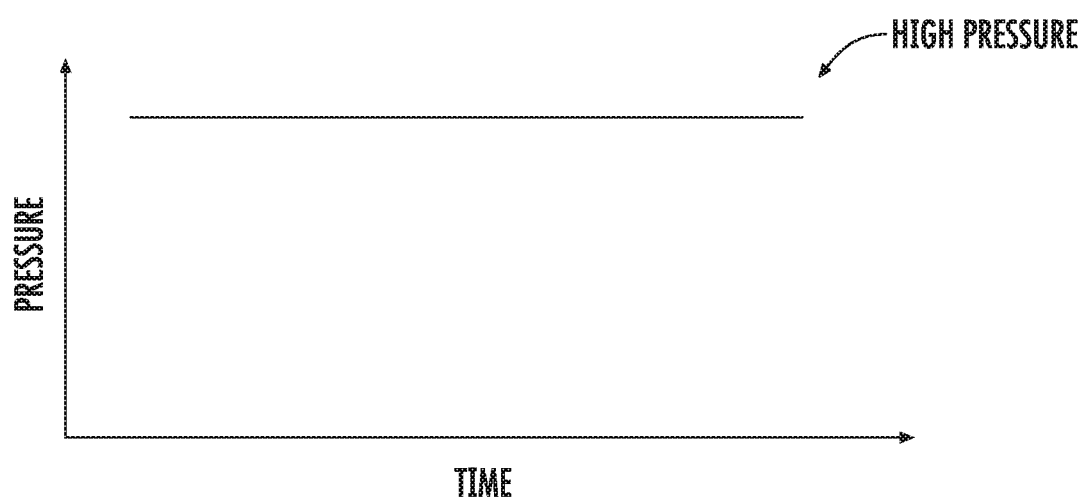
FIG. 26 is a graph of a quality flow test pressure data against time.

As indicated above, after the substrate 112 is formed, preferably, only the test holes 118 are formed in the substrate 112. A baseline flow test may be conducted by introducing a test liquid 122 such as water into the test holes 118 and measuring at least one baseline flow characteristic (e.g., flow rate and pressure). In particular, a mechanical packer 28 may be inserted into the test hole 118. A test liquid such as water 120 may be injected into the test holes 118 via the mechanical packer while under a constant pressure. The baseline flow characteristic of flow rate of water and pressure of water is read and recorded. The flow rate and the pressure of water may define a permeability of the substrate 112. Before sealing the substrate 112, it is expected that the substrate 112 may have a high flow rate as shown in FIG. 23 and a low pressure as shown in FIG. 24. After the sealing step, the flow characteristic is taken again to determine the permeability of the substrate 112. Preferably, the permeability decreases after sealing step.

After the baseline flow characteristic is red, the mechanical packers 28 are removed from the test holes 118. The test holes 118 are then plugged so that the filling substance 122 is not introduced into the test holes 118 as the filling substance 122 is injected into the filling holes 116.

After the test holes 118 are filled with the plug to prevent the filling substance 122 from being introduced into the test holes 118, the user then proceeds to fill the substrate 112. In particular, a mechanical packer 28 may be inserted into the fill holes 116 to inject the filling substance 122 into the substrate 112. The filling substance 122 may be pumped from the filling substance source into the fill holes 116 via a high pressure pump. The filling substance may be polyurethane, epoxy, polyacrylate, or microfine cement sold under the tradename ALCHEMY-SPETEC. The filling substance 122 is injected through the channels 170 and the voids 172 under pressure. The goal is to push the filling substance 122 throughout all of the channels 170 and voids 172. Since the channels 170 and voids 172 interconnect with each other in the substrate 112, the filling substance fills all of the pathways that allows water or liquid to pass from one side of the substrate to the other side of the substrate 112. This decreases permeability of the substrate 112. After the filling substance 122 is injected into all of the fill holes 116, the user may remove the plugs from the test holes 118. The mechanical packer 128 is then inserted into the test holes 118 and the test liquid is then pumped into the test holes 118 to re-measure the permeability of the substrate 112. In particular, the flow rate and the pressure under which the liquid flows through the test holes 118 is measured and recorded. If the ratio between the flow rate and the pressure after the filling step is lower than the ratio of flow rate and pressure during the baseline flow test, then the permeability of the substrate 112 has been reduced. The flow rate over pressure provides a quantifiable measure of the improved permeability of the substrate 112 via the sealing step. Other definitions of permeability may be utilized. By way of example and not limitation, a permeability may be measured as the flow rate under a constant predetermined pressure. If the flow rate is reduced as shown by a comparison before and after the sealing step, then permeability is reduced.

In another application, the testing procedure described herein may be utilized in relation to a substrate that has injection tube waterstops pre placed in the substrate when the substrate was formed. Put simply, since concrete is prone to cracking and leaking, concrete workers may place injection tube waterstops at the time of forming the substrate. When the substrate leaks, injection leak sealing material can be injected into the injection tube waterstops. In these substrates, the test holes 18, 118 may be drilled into the exterior surface of the substrate. These test holes 18, 118 may be used to measure a baseline flow test before injecting the leak sealing material and a quality flow test after curing of the leak sealing material. Based on flow characteristics (e.g., flow rate, flow pressure or a combination of the two), the effectively of injecting the leak seal material into the injection tube waterstops may be measured.

Referring now to the embodiment described in relation to FIGS. 1-26, the distance between the fill holes 16 with each other and the distance between the test holes 18 with each other may vary based on the circumstances. By way of example and not limitation, the fill holes 16 and the test holes 18 may be between 2 inches and 120 inches apart from each other. If a hairline crack is being sealed, then the fill and test holes 16, 18 may be spaced apart 2 inches away from each other. On the other hand, if the crack is very large, then the fill and test holes 16, 18 may be spaced apart 120 inches away from each other. If the substrate is still leaking in a particular area, then the seal can be injected into new ports which are spaced apart closer to each other than before where the liquid is still leaking on the substrate. Also, in a cold joint application (i.e., where concrete is poured on existing concrete), the leakage in such an application may be more predictable. As such, the spacing between the fill and test holes 16, 18 may be large. If we have a large crack or joint that spans long distances, the spacing between the fill and test holes 16, 18 may be up to 120 inches.

Moreover, for the porosity procedure described in relation to FIGS. 27 and 28, different substrates (e.g., shotcrete, masonry, brick) may require smaller or larger spacing between the fill and test holes 116, 118. By way of example and not limitation, in a basement application, the fill and test holes 116, 118 may be about 2 to 4 inches apart from each other. On the other hand, on a bridge project, the spacings between the test holes 116, 118 may be 20 to 40 feet apart from each other. The fill holes 116 may be spaced apart as described above in relation to embodiment shown in FIGS. 1-26.

The particulars shown herein are by way of example only for purposes of illustrative discussion and are not presented in the cause of providing what is believed to be most useful and readily understood description of the principles and conceptual aspects of the various embodiments of the present disclosure. In this regard, no attempt is made to show any more detail than is necessary for a fundamental understanding of the different features of the various embodiments, the description taken with the drawings making apparent to those skilled in the art how these may be implemented in practice.

What is claimed is:

1. A method of testing effectiveness of a sealing procedure on a concrete structure, the method comprising the steps of:
    forming a first drill hole in the concrete structure, the first drill hole extending into the concrete structure from a first surface, the first drill hole having an end at the first surface;
    forming a test drill hole in the concrete structure in spaced relation to the first drill hole, the test drill hole extending into the concrete structure from the first surface, the test drill hole having an end at the first surface spaced from the end of the first drill hole;
    determining a baseline flow rate and a baseline pressure of a test liquid by directing the test liquid into the test drill hole;
    plugging the test drill hole with a plug so that a filling substance does not enter the test drill hole when the filling substance is injected into the first drill hole;
    injecting the filling substance into the first drill hole under pressure so that the filling substance seeps into the concrete structure to fill channels in the concrete structure;
    after the injecting step, removing the plug from the test drill hole;
    following hardening of the filling substance in the channels of the concrete structure and the removing step, determining a quality flow rate and a quality pressure by directing the test liquid into the test drill hole.

2. The method recited in claim 1, further comprising the step of comparing the baseline flow rate and the baseline pressure to the quality flow rate and the quality baseline pressure to determine an effectiveness of the injecting step.

3. The method of claim 1 wherein the step of forming the test drill hole and the first drill hole comprising the step of forming the holes about 40% to 60% of a thickness of the concrete structure.

4. The method recited in claim 1, wherein the steps of forming the first drill hole and the test drill hole includes the steps of drilling the first and test drill holes into the concrete structure at an angle perpendicular to the first surface.

5. The method recited in claim 1, wherein the step of determining a quality flow rate and quality pressure includes directing water into the test drill hole.

6. The method recited in claim 5, further comprising the step of comparing a baseline ratio, $Q_1/P_1$, to a quality ratio, $Q_2/P_2$ wherein $Q_1$ is the baseline flow rate, P1 is the baseline pressure, Q2 is the quality flow rate and P2 is the quality pressure.

7. The method of claim 1 wherein the first drill hole and the test hole is about 6 inches to 18 inches apart.

8. The method of claim 1 further comprising the step of forming a second drill hole in the concrete structure, the second drill hole being 6 inches to 18 inches apart from the first drill hole.

9. The method of claim 8 wherein the first and second drill holes are adjacent to each other so that the filling substance injected into the first drill hole travels more than ½ a distance between the first and second drill holes.

10. The method of claim 8 wherein the first and second drill holes are parallel to each other.

11. The method of claim 8 wherein the first and second drill holes each have an inner diameter between 0.2 inches and 3 inches.

12. The method of claim 7 wherein the first drill hole and the test drill hole are parallel to each other.

13. The method of claim 1 wherein the injecting step fills the channels within the concrete structure starting from within the concrete structure.

* * * * *